United States Patent [19]

Kreamer

[11] Patent Number: 5,370,623
[45] Date of Patent: Dec. 6, 1994

[54] CATHETER WITH PROTECTIVE COVER AND METHOD OF CATHETERIZATION

[76] Inventor: Jeffry W. Kreamer, 782 W. Euclid, Palatine, Ill. 60067

[21] Appl. No.: 24,351

[22] Filed: Mar. 1, 1993

[51] Int. Cl.⁵ ............................................. A61M 5/178
[52] U.S. Cl. ..................................... 604/165; 604/198
[58] Field of Search ............... 604/164, 165, 170, 264, 604/168, 117, 93, 161, 110, 192, 198

[56] References Cited

U.S. PATENT DOCUMENTS

| | | | |
|---|---|---|---|
| 3,727,613 | 4/1973 | Sorenson et al. | 604/165 |
| 4,713,057 | 12/1987 | Huttner et al. | 604/264 |
| 4,762,516 | 8/1988 | Luther et al. | 604/168 |
| 4,850,961 | 7/1989 | Wanderer | 604/198 |
| 4,861,334 | 8/1989 | Nawaz | 604/164 |
| 4,944,728 | 7/1990 | Carrell et al. | 604/164 |
| 4,994,042 | 2/1991 | Vadher | 604/165 |
| 5,019,049 | 5/1991 | Haining | 604/165 |
| 5,104,382 | 4/1992 | Brinkerhoff | 604/165 |
| 5,186,712 | 2/1993 | Kelso et al. | 604/165 |
| 5,269,761 | 12/1993 | Stehrenberger | 604/198 |
| 5,279,590 | 1/1994 | Sinko | 604/198 |

*Primary Examiner*—John G. Weiss
*Attorney, Agent, or Firm*—Kent A. Herink; Brian J. Laurenzo; Brett J. Trout

[57] ABSTRACT

A catheterization system for embedment in a patient includes a sharp edged needle at the proximal end portion of the catheter. A protective sheath is received about the needle for relative slidable movement thereon between a first position wherein the sharp edge of the needle extends beyond the protective sheath and a second position wherein the blunt leading proximal edge of the protective sheath extends beyond and covers the sharp edge of the needle.

5 Claims, 2 Drawing Sheets

FIG. 1
FIG. 2
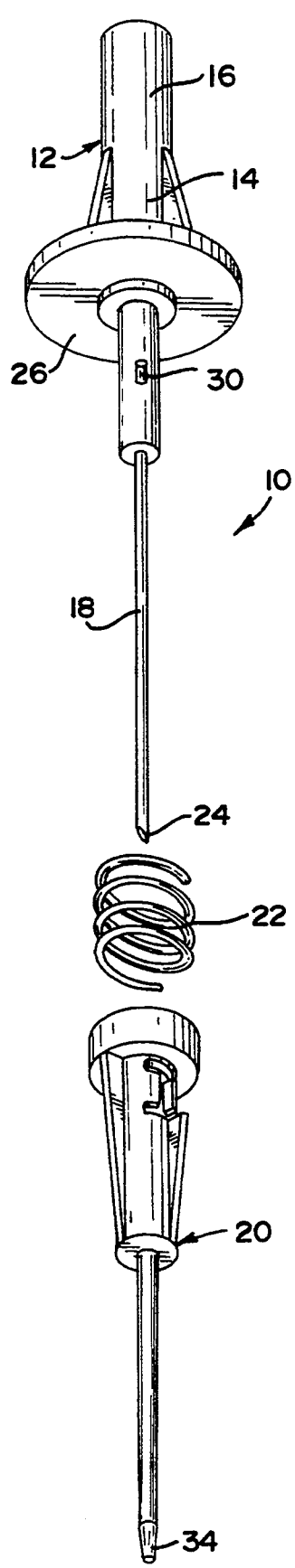
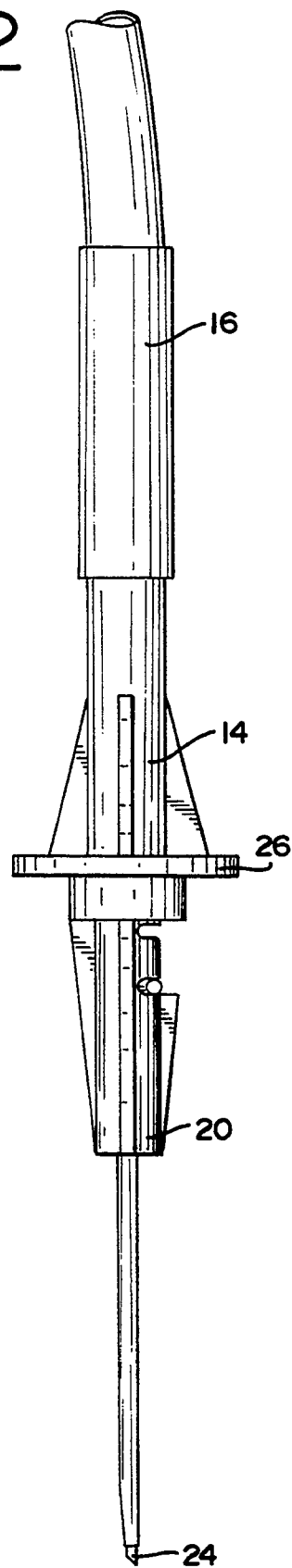

CATHETER WITH PROTECTIVE COVER AND METHOD OF CATHETERIZATION

BACKGROUND OF THE INVENTION

The invention relates generally to catheters and, more specifically, to a catheter having a protective cover that protects the sharp edge after insertion of the catheter into the body of a patient.

Many current medical practices involve gaining access to a body cavity or blood vessel by the penetration of tissues with a sharp edged instrument, most typically a needle. The sharp edged instrument may be used to obtain a tissue sample. In other situations, the sharp edged instrument is replaced by a blunt edged catheter which may remain in the body for an extended period of time.

The procedure for inserting a catheter into a blood vessel is usually performed using the Seldinger technique wherein a sharp edged needle is used to penetrate the tissues and into the blood vessel, a guide wire is inserted through the needle into the vessel, the needle is removed, and a catheter having a blunt edge is advanced along the guide wire and into the vessel.

The sharp edged instrument cannot be left in the body for any extended period of time due to the potential for trauma from the sharp edge. A catheter may be used, for example, to drain fluid from the chest cavity. Embedding a sharp edged needle would pose a risk of penetrating and collapsing a lung.

While the Seldinger technique does provide a method for insertion of a blunt edged catheter that remains in the body, it is complex, cumbersome, and time consuming to perform. In addition, the multiple parts involved in the Seldinger technique result in increased waste of sterile supplies and is expensive. There is, accordingly, a need for a catheterization system which is simpler and faster to use, less expensive, and results in less waste than known systems.

SUMMARY OF THE INVENTION

The present invention consists of a catheter that includes a sharp edge for penetrating bodily tissues and means for covering the sharp edge after the catheter has reached its intended position. In a preferred embodiment of the invention, a tubular sheath is received about the proximal, sharp edged end of a catheter. The sheath is initially held in a retracted position wherein the sharp edge of the catheter is exposed. Upon insertion of the catheter to the intended position in a patient, the sheath is slidably advanced proximally on the catheter to a position overlying and covering the sharp edged end portion of the catheter.

The present invention offers improved and safer catheterization methods. For example, in the catheterization of a body cavity, once the exposed sharp edge of the catheter has penetrated overlying tissues and reached the desired cavity, the protective cover can be advanced beyond the sharp edge to permit adjustment and maneuvering of the catheter with a much reduced risk of further undesirable injury to adjacent tissues. In another example, blood flow through a vessel which is the subject of a surgical procedure could be occluded using a catheter of the present invention which included a balloon. The catheter with the sharp edge pierces the wall of the vessel, the protective cover is moved to cover the sharp edge and then the catheter advanced to appropriately position the balloon. The protective cover acts to prevent trauma to the vessel during advancement of the catheter. In a third example, only a single catheter of the present invention would be required in the performance of an angiogram. The artery is cannulated with the sharp edge, which is then covered, and the catheter is advanced to the site for dye injection. In contrast, current angiographic procedures require a sharp edged catheter, a guide wire and a blunt edge catheter for advancement in the artery and dye injection, using the Seldinger technique.

The invention provides a simpler catheterization system by requiring only a two step insertion process using an integrated catheter system wherein the sharp edge is used to penetrate bodily tissues followed by advancement of a protective sheath.

The reduced number of steps also makes the present invention a faster catheterization system over the prior art systems.

A catheter in accordance with the present invention will be less expensive to manufacture in its two principal parts in comparison to the three distinct elements of the Seldinger technique.

The object of reducing sterile supply waste is achieved in that the present invention is packaged and used as a self-contained, unitary system. In contrast, the prior art systems have multiple distinct elements each of which is often separately packaged.

These and other objects of the invention will be made clear to one skilled in the art upon a review of the accompanying drawings, description and claims.

BRIEF DESCRIPTION OF THE DRAWINGS

FIG. 1 is an exploded perspective view of the catheterization system of the present invention.

FIG. 2 is a side elevational view of the catheterization system of FIG. 1.

DETAILED DESCRIPTION OF A PREFERRED EMBODIMENT

Figure 3:
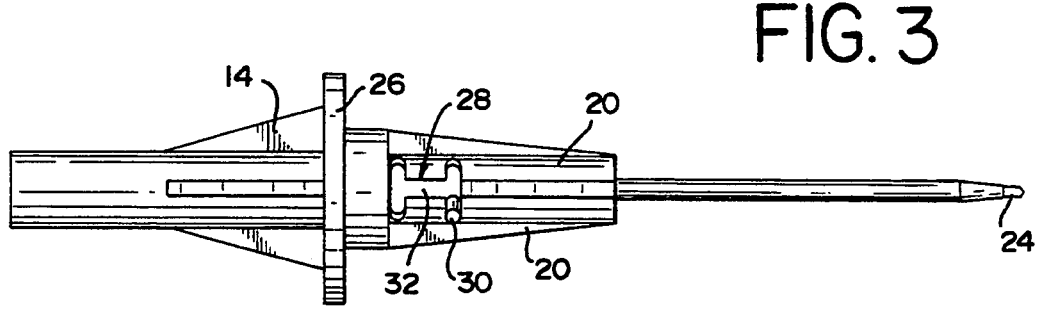
FIG. 3 is a top elevational view corresponding to FIG. 2 wherein the sharp edge of a needle of the catheterization system is exposed at the proximal end thereof.

While the preferred embodiment illustrated in the drawings and described herein is a catheter of the type typically used for the intravenous administration of fluids, it will be understood by those skilled in the art that sharp edged needles are utilized in a wide variety of medical procedures wherein a tubular member is introduced into the body of a patient, and that the present apparatus may be used in virtually all of such medical practices. Examples include catheters for intravenous feeding, catheters for the drawing of blood or other somatic tissues, chest tubes, balloon catheters, catheters for conducting angiograms, and the like.

Referring now to FIG. 1 there is illustrated, generally at 10, a catheterization system of the present invention. A catheter 12 includes at its proximal end portion a hand-graspable support member 14 which receives a first tubular member 16 extending distally thereof. Opposite of the first tubular member 16, a needle 18 extends proximally of and is supported by the hand-graspable support member 14. The needle terminates with the customary sharp edge 24 for the piercing of bodily tissues.

The catheterization system 10 includes a protective sheath 20 and a compression spring 22 that are received about the needle 18 and support member 14.

In assembly relation, as illustrated in FIG. 2, the needle 18 extends axially of the protective sheath 20 such that, when the protective sheath 20 is in a retracted position therefor, the sharp edge 24 of the needle 18 extends beyond the proximal end portion of the protective sheath 20. In its retracted position, the distal end portion of the protective sheath 20 rests against an enlarged ring member 26 of the support member 14.

Figure 4:
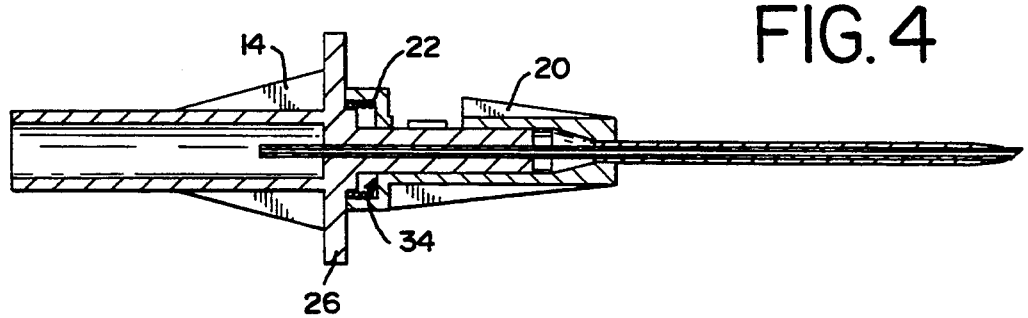
FIG. 4 is a cross sectional view taken along line 4—4 of FIG. 3.
Figure 5:
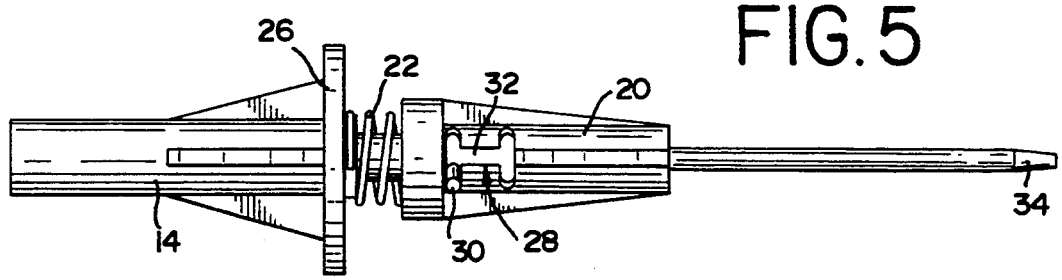
FIG. 5 is a top elevational view of the catheterization system wherein a protective sheath is shown in the extended position covering the sharp edge of the needle.
Figure 6:
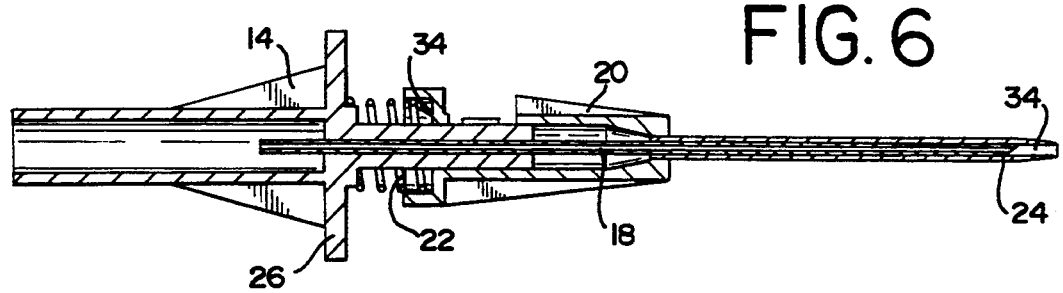
FIG. 6 is a cross sectional view taken along line 6—6 of FIG. 5.

As best illustrated in FIGS. 1, 3, and 5, the protective sheath 20 includes an I-shaped key way 28 which operates in conjunction with a corresponding key or pin 30 that projects radially from the support member 14 between the needle 18 and the enlarged ring member 26. Movement of the protective sheath 20 relative to the support member 14 is thus constrained by the movement of the pin 30 inside the confines of the I-shaped key way 28. When the protective sheath 20 is in its retracted position (FIG. 3), the protective sheath 20 is held against relative axial movement unless the protective sheath 20 has been pivoted so as to align the pin 30 and the longitudinal channel section 32 of the key way 28. The spring 22 is held in compression between the expanded ring member 26 and a coacting radial wall 34 of the protective sheath 20 (FIGS. 4 and 6). Accordingly, if the protective sheath 20 is in the retracted position, pivotal movement of the retractive sheath 20 to align the pin 30 and the central channel portion 32 of the key way 28 will, unless restrained, permit the spring 22 to move the protective sheath 20 proximally to an extended position (FIGS. 5 and 6).

In the extended position, the protective sheath 20 is pivotable in either direction relative to the central channel section 32 of the key way 28. The key way 28 and pin 30 thus operate to permit the protective sheath 20 to be releasably held in the extended position (FIGS. 5 and 6) wherein the sharp edge of the needle 18 is inside the protective sheath 20.

Since the proximal end portion 34 of the protective sheath 20 is rounded or blunt, it is much less likely to pierce or damage bodily tissues than the sharp edge of the needle 18 which has been retracted inside the protective sheath 20. It is seen, accordingly, that the catheterization system 10 provides both a sharp edged needle for piercing bodily tissues, for example in the cannulization of a vessel, and a self-contained, extensible and retractable protective sheath for effectively covering and disabling the sharp edge of the needle so that the catheterization system 10 can be left in residence inside the body or manipulated to a variety of sites, without further risk of injury due to unwanted contact of bodily tissues with the sharp edge of the needle.

In use of the catheterization system 10, a health practitioner would initially pivot the protective sheath 20 so as to align the pin 30 with the central channel section 32 of the key way 28 and, compressing the string 22, move the protective sheath 20 distally relative to the support member 14. The practitioner could then pivot the protective sheath 20 so as to move the pin 30 into one of the proximal pair of circumferentially extending leg sections of the I-shaped key way 28. This will serve to restrain the protective sheath 20 in the retracted position wherein the sharp edge 24 of the needle 18 is exposed. The practitioner would then manipulate the catheter system 10 to use the exposed sharp edge 24 of the needle 18 to puncture the bodily tissues of a subject patient as called for in the procedure being practiced. Once the catheterization system 10 has been moved to the desired position, the health practitioner would pivot the protective sheath 20 so as to again align the pin 30 and central channel section 32 of the key way 28. Upon a release of restraining pressure on the protective sheath 20, the spring 22 would extend the protective sheath 20 to the extended position wherein the sharp edge of the needle 18 would be protected inside the protective sheath 20. The protective sheath 20 could then pivoted in either direction to move the pin 30 into one of the distal pair of circumferentially extended leg sections of the key way 28.

The catheterization system 10, once inserted, may be adjusted in position as desired by the health practitioner in two distinct configurations. If the proximal end of the catheterization system is to be moved inside the patient wherein further puncturing of the bodily tissues is not desired, the protective sheath 20 may be kept in its extended position while the catheter system 10 is manipulated to the desired new location.

Alternatively, if a readjustment in the position of the catheterization system 10 is desired which calls for the addtitional puncturing of bodily tissues, the protective sheath 20 is retracted to expose the sharp edge 24 of the needle 18 and the desired manipulation of the catheterization system is performed. Once the catheterization system 10 has reached the adjusted position, the protective sheath 20 is moved to its extended position covering the sharp edge of the needle 18.

While the preferred embodiment has been described as including a compression spring, the catheterization system can be constructed and used without such a spring. Further, although an I-shaped key way is described, other shapes of key ways, particularly a C-shaped or J-shaped key way could be utilized.

Although the invention has been described with respect to a preferred embodiment thereof, it is to be also understood that it is not to be so limited since changes and modifications can be made therein which are within the full intended scope of this invention as defined by the appended claims.

I claim:

1. A method of catheterization of a patient, comprising the steps of:
    (a) inserting into the patient a first tubular member having a proximal end portion with a sharp edge;
    (b) providing a second, coaxial tubular member which is received about said first tubular member and which includes a proximal end portion having a blunt edge;
    (c) advancing said second tubular member from a first position wherein said sharp edge extends beyond said second tubular member and a second position wherein said second tubular member covers said sharp edge; and
    (d) means for holding said second, coaxial tubular member in said second position.

2. A method as defined in claim 1, further comprising a step of biasing said second tubular member from said first position toward said second position.

3. A method as defined in claim 2, further comprising a step of releasably returning said second member to said first position thereby preventing movement by said biasing step until released.

4. A method as defined in claim 1, further comprising a step of maneuvering the position of said first tubular member inside the patient following advancement of said second tubular member.

5. A method of catheterization of a patient, comprising the steps of:
   (a) inserting into the patient a first tubular member having a proximal end portion with a sharp edge;
   (b) providing a second, coaxial tubular member which is received about said first tubular member and which includes a proximal end portion having a blunt edge;
   (c) advancing said second tubular member from a first position wherein said sharp edge extends beyond said second tubular member and to a second position wherein said second tubular member covers said sharp edge;
   (d) maneuvering said first tubular member inside the patient;
   (e) retracting said second tubular member to expose said sharp edge;
   (f) maneuvering said first tubular member inside the patient; and
   (g) advancing said second tubular member to cover said sharp edge.

* * * * *